United States Patent [19]

Kojima et al.

[11] Patent Number: 5,486,458
[45] Date of Patent: Jan. 23, 1996

[54] METHOD OF QUANTITATIVE ASSAY FOR 1,5-ANHYDROGLUCITOL

[75] Inventors: Ryo Kojima; Yoshiro Sato, both of Koriyama; Takeshi Nagasawa, Urawa, all of Japan

[73] Assignee: Nitto Boseki Co., Ltd., Fukushima, Japan

[21] Appl. No.: 85,317

[22] Filed: Jun. 30, 1993

[30] Foreign Application Priority Data

Jun. 30, 1992 [JP] Japan .................................. 4-172955

[51] Int. Cl.$^6$ .............................. C12Q 1/54; C12N 1/00
[52] U.S. Cl. .................. 435/14; 435/25; 435/26; 435/28; 435/39; 435/98; 435/105; 435/810; 435/832; 435/911; 436/174; 436/175
[58] Field of Search .................. 435/14, 25, 26, 435/28, 39, 98, 105, 810, 832, 911, 975; 436/174, 175

[56] References Cited

U.S. PATENT DOCUMENTS

| 4,810,640 | 3/1989 | Nakamura et al. | |
| 4,994,377 | 2/1991 | Nakamura et al. | 435/25 |

FOREIGN PATENT DOCUMENTS

| 0261591A2 | 3/1988 | European Pat. Off. | |
| 61-239886 | 10/1986 | Japan | C12N 9/04 |
| 2-42980 | 2/1990 | Japan | C12N 9/04 |

OTHER PUBLICATIONS

Fukumura et al, *Clinical Chemistry*, vol. 21, pp. 43–48, 1992 (Japanese with English summary on p. 48).
Suzuki et al, *Starch/Staerke*, vol. 39, No. 8, pp. 271–273, 1987.
Tanaka et al, *Chemical Abstracts*, vol. 113, p. 358, Ref. No. 187608w, 1990.
Nakamura et al, *Chemical Abstracts*, vol. 114, p. 389, Ref. No. 243490v, 1991.
Fukumura et al, *Chemical Abstracts*, vol. 118, p. 321, Ref. No. 18642a, 1993.
Yabuuchi et al, *Clin. Chem.* vol. 35, No. 10, pp. 2039–2043, 1989.
Fukumura et al, *Clin. Chem.*, vol. 38, No. 12, pp. 2553–2554, 1992.
*Chemical Patents Index, Documentation Abstracts Journal D*, Derwent Publications 1990; No. 90–161279/21, JO 2104–298–A, Oct. 13, 1988.
Fukumura, Yukihito et al., "Interference of Maltose for the Determination of 1,5–Anhydroglucitol with Lana AG$^\epsilon$ Kit", Rhinsho Kagku (Nippon Rinsho Kagaki), 21 (1992), pp. 43–48.

*Primary Examiner*—Michael G. Wityshyn
*Assistant Examiner*—Abdel A. Mohamed
*Attorney, Agent, or Firm*—Darby & Darby

[57] ABSTRACT

There is provided a method of quantitative assay for 1,5-anhydroglucitol in a specimen characterized by effectively removing maltose present in the specimen using α-glucosidase. Maltose present in a specimen is previously converted into glucose by the action of α-glucosidase derived from a microorganism belonging to the genus Bacillus to remove the affect by maltose. Then 1,5-anhydroglucitol in the specimen is quantitatively determined.

7 Claims, 11 Drawing Sheets

1,5-AG CALIBRATION CURVE

GLUCOSE REMOVAL ABILITY

METHOD OF QUANTITATIVE ASSAY FOR 1,5-ANHYDROGLUCITOL

FIELD OF THE INVENTION

The present invention relates to a method of enzymatic assay for 1,5-anhydroglucitol (hereafter referred to as "1,5-AG"), which is expected as a marker for diagnosis of diabetes, in a simple and rapid way. This method is also applicable to an automated analysis device.

BACKGROUND OF THE INVENTION

RELATED ART STATEMENT 1,5-AG is a compound which is present in the cerebrospinal fluid and plasma of humans. It is reported that its quantity is markedly reduced in plasma collected from patients with certain diseases, particularly with diabetes (Yasuo Akanuma, Kazuyuki Tobe, Nippon Naikagakkai Zasshi (Journal of Japanese Internal Medicine Association), 80, 1198–1204, 1991). 1,5-AG is thus expected to be as a marker for diagnosis of diabetes.

As practical assay for 1,5-AG in a specimen, there is known a method which comprises removing sugars present in the specimen other than 1,5-AG, using an ion exchange column chromatography after deproteinization of the specimen; then oxidizing 1,5-AG with pyranose oxidase (hereafter abbreviated as PROD) or L-sorbose PROD) or L-sorbose oxidase and quantitatively determining hydrogen peroxide formed (Japanese Patent KOKAI (Laid-Open) No. 63-185397; hereinafter such a method is referred to as column enzyme method).

Serum or plasma collected from the patient with diabetes is mainly a specimen to be assayed for 1,5-AG. In blood from the patient with diabetes, its glucose concentration is higher than that of normal person. In blood from normal person, the glucose concentration is in the range of approximately 60 to 100 mg/dl, whereas in blood from the patient with diabetes, the glucose concentration is widely distributed in the range of 100 to 1000 mg/dl. On the other hand, the concentration of 1,5-AG in blood is in the range of 1.64 to 2.68 mg/dl for normal person but in the patient with diabetes its concentration is as extremely low as 0.18 to 0.21 mg/dl (Nippon Rinsho (Japanese Clinic), 47, 1989, extra issue, Immunological Inspection in Blood and Urinary Chemical Test over Wide Range; first volume, 439–442, Kawai). Therefore, the concentration of 1,5-AG in blood from the patient with diabetes becomes about 1/470 or less. In addition, glucose is structurally similar to 1,5-AG so that it is impossible to selectively assay for 1,5-AG in the presence of glucose and 1,5-AG in the current state of the art. It is thus essentially required to selectively remove glucose or pretreat specimen by adequately modifying glucose.

In the column enzyme method, proteins and endogenous sugars other than 1,5-AG must be removed and extremely complicated operations for the removal are disadvantageous for the column enzyme method. Furthermore, maltose-added lactate Ringer's solution is often applied as infusion to the patient with diabetes for the purpose of supplementing calorie source, supplementing and compensating for fluid outside tissue in reduced volume of circulated blood and tissue fluid, or correcting metabolic acidosis. In this case, maltose increases in blood of the patient with diabetes. It is reported that maltose present in a specimen collected from such a patient with diabetes cannot be fully removed even by a separation column and hence, there is a serious positive error in measurement data of 1,5-AG ("Rinsho Kagaku (Clinical Chemistry)", 21, 43–48, 1992).

SUMMARY OF THE INVENTION

An object of the present invention is to solve the problem caused by endogenous maltose which was the shortcoming in the conventional column enzyme method and provide a method of quantitative assay for 1,5-AG which is applicable to an automated analysis equipment.

Another object of the present invention is to provide a method of quantitative assay for 1,5-AG which eliminates the problem caused by endogenous maltose and solve the defect of complicated operations in conventional column enzyme method, and a kit used for the method.

In order to solve the foregoing problems, the present inventor has made extensive investigations and as a result, found that 1,5-AG can be accurately determined without being affected by endogenous maltose, by previously reacting maltose present in a specimen with α-glucosidase derived from a microorganism belonging to the genus Bacillus, upon quantitative determination of 1,5-AG using PROD, to convert maltose into glucose, then selectively remove the glucose together with sugars other than 1,5-AG present in the specimen, and then assaying for 1,5-AG.

It has also been found that in a method of quantitative assay for 1,5LAG in a specimen using PROD, the method which comprises converting maltose present in the specimen into glucose by the action of α-glucosidase derived from a microorganism belonging to the genus Bacillus, phosphorylating said glucose by hexokinase (hereafter referred to as HK) and an excess amount of adenosine-5'-triphosphate (hereafter referred to as ATP) in the pH range of 7.2 to 8.5 thereby to selectively remove the glucose together with sugars other than 1,5-AG present in the specimen; and then reacting 1,5-AG in the specimen with PROD to quantitatively assay for 1,5-AG, the phosphorylation and the reaction between 1,5-AG and PROD are performed in the pH range of 7.2 to 8.5, or PROD derived from *Basidiomycetous fungi* No. 52 is used as PROD, whereby the phosphorylation can be readily carried out using an excess amount of ATP and the reaction of 1,5-AG with PROD proceeds in the presence of excess ATP as it is, so that 1,5-AG can be assayed without PROD being inhibited by ATP. It has thus been found that 1,5-AG can be quantitatively determined rapidly in an extremely simple manner and the method of quantitative assay for 1,5-AG is applicable to an automated analysis device. The present invention has been accomplished based on these findings.

A first aspect of the present invention lies in a method of quantitative assay for 1,5-AG in a specimen using PROD, which comprises:

converting maltose present in the specimen into glucose by the action of α-glucosidase derived from a microorganism belonging to the genus Bacillus;

selectively remove the glucose together with sugars other than 1,5-AG present in the specimen so that 1,5-AG remains in the specimen;

and then quantitatively determining 1,5-AG in the specimen using PROD.

A second aspect of the present invention lies in a method of quantitative assay for 1,5-AG in a specimen using PROD, which comprises:

converting maltose present in the specimen into glucose by the action of α-glucosidase derived from a microorganism belonging to the genus Bacillus;

phosphorylating the glucose by HK and an excess amount of ATP in the pH range of 7.2 to 8.5 thereby to selectively remove the glucose together with sugars other than 1,5-AG present in the specimen so that 1,5-AG remains in the specimen;

and then reacting 1,5-AG in the specimen with PROD as it is, in the pH range of 7.2 to 8.5 to quantitatively assay for 1,5-AG.

A third aspect of the present invention lies in a method of quantitative assay for 1,5-AG in a specimen using PROD, which comprises:

converting maltose present in the specimen into glucose by the action of α-glucosidase derived from a microorganism belonging to the genus Bacillus;

phosphorylating the glucose by HK and an excess amount of ATP in the pH range of 7.2 to 8.5 thereby to selectively remove the glucose together with sugars other than 1,5-AG present in the specimen so that 1,5-AG remains in the specimen;

and then reacting 1,5-AG in the specimen with PROD derived from *Basidiomycetous fungi* No. 52, as it is, to quantitatively assay for 1,5-AG.

A fourth aspect of the present invention lies in a kit used for quantitative assay for 1,5-AG in a specimen comprising the following reagents:

(1) α-glucosidase derived from a microorganism belonging to the genus Bacillus;

(2) HK;

(3) ATP; and, (4) PROD.

DETAILED DESCRIPTION OF PREFERRED EMBODIMENTS

Figure 1:
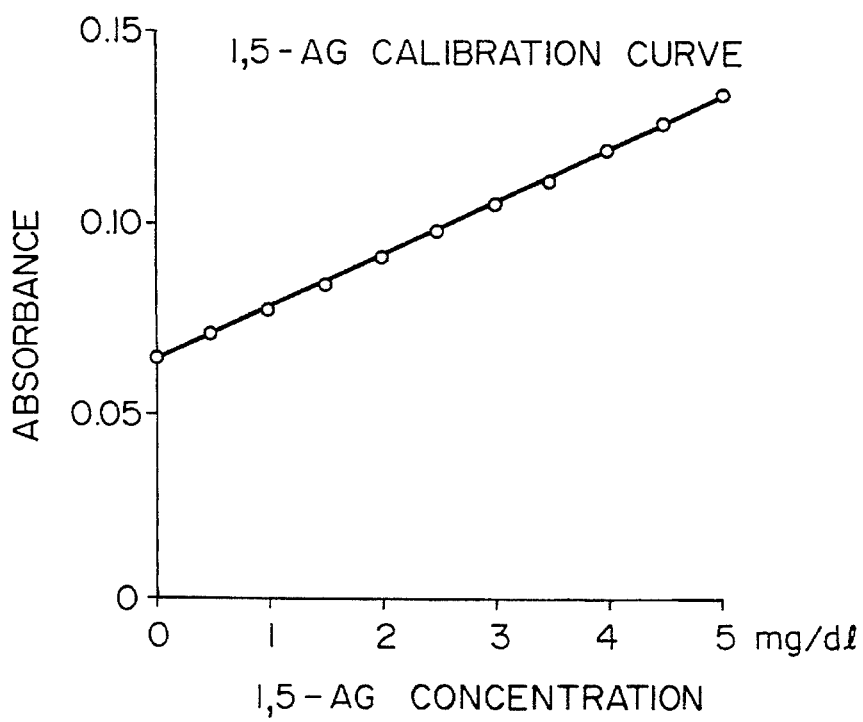
FIG. 1 is a graph showing quantitative property of 1,5-AG where Reagent 1-A (no maltose hydrolase is added) is used.

Hereinafter the present invention will be described in detail.

The specimen in the present invention is used to mean any specimen; there is no particular restriction on the specimen so long as the concentration of 1,5-AG in the specimen is intended to determine. For example, there are serum, plasma, etc. as described above.

According to the quantitative assay for 1,5-AG of the present invention, α-glucosidase is reacted firstly with maltose present in a specimen to convert maltose into glucose. In order to avoid the influence by endogenous maltose inherently present in a specimen and apply the quantitative assay for 1,5-AG to a general purpose automated analysis device, it is mandatorily required to convert maltose in the specimen into glucose in a short period of time and erase the glucose in a short period of time.

As a result of extensive investigations, the present inventor has found that α-glucosidase derived from a microorganism belonging to the genus Bacillus shows a high affinity to and reactivity with maltose as compared to known α-glucosidase, e.g., α-glucosidase derived from Saccharomyces sp. or glucoamylase derived from Rhizopus sp. and can thus convert maltose in a specimen into glucose rapidly. In particular, α-glucosidase derived from *Bacillus stearothermophilus* is preferred. This α-glucosidase can be obtained from, e.g., *Bacillus stearothermophilus* ATCC 12016 according to the process described in Starch/Staerke, 39(8), 271–273 (1987). The α-glucosidase is commercially available on the market, e.g., under the trademark of Toyobo Code No. AGH-211.

The α-glucosidase derived from *Bacillus stearothermophilus* possess the following physicochemical properties.

(1) Appearance: white powder (lyophilized)
(2) Molecular weight: about 62,000 when measured by gel filtration and SDS-gel electrophoresis
(3) Isoelectric point: 5.2
(4) Michaelis' constant: $5.7 \times 10^{-4}$M (p-nitrophenyl-α-glucose)
(5) Inhibitor: heavy metal ions ($Fe^{2+}$, $Ca^{2+}$)
(6) Optimum pH: 6–7
(7) pH stability; 7–8
(8) Thermal stability: stable at 60° C. or lower (pH 7.0, 15 minutes)

An amount of α-glucosidase used to react with maltose in a specimen is an amount to hydrolyze maltose in a specimen to glucose. It is generally 1 U/ml or more, preferably 5 U/ml or more, more preferably, 10 U/ml or more. Upon the actual measurement, α-glucosidase is used generally in an amount of 20 to 100 U/ml. There is no particular restriction on the pH in the reaction with α-glucosidase but any pH range may be chosen so long as the pH range is appropriate for the action of α-glucosidase. For simplicity of operation, it is preferred to react α-glucosidase in the same pH range as the range used for the phosphorylation subsequent thereto, namely, convert maltose into glucose by the action of α-glucosidase, and selectively removing the glucose through the phosphorylation by HK and ATP, together with other sugars present in the specimen. As will be later described, it is preferred to act α-glucosidase on maltose in a specimen in the pH range for the phosphorylation, for example, in the pH range of 7.2 to 8.5 or 6 to 9. As a temperature, room temperature is generally appropriate for the reaction with α-glucosidase.

After maltose present in a specimen is converted into glucose, the glucose is selectively removed together with sugars other than 1,5-AG present in the specimen in such a manner that 1,5-AG remains (hereafter this selective removal is sometimes referred to as a first step reaction). The term "sugars other than 1,5-AG present in a specimen" is used to mean mainly glucose but also covers other sugars phosphorylated by HK, for example, fructose, 5-keto-D-fructose, mannose, 2-deoxyglucose, glucosamine, etc.

For the selective removal of the sugars other than 1,5-AG present in a specimen, it is preferred to choose a method which can erase sugars such as glucose, etc. in a reaction solution without relying on any solid phase, for the purpose of applying to an automated device for analysis. As such methods, there are known acid decomposition of sugars with 6N hydrochloric acid, reduction of sugars with sodium borohydride, conversion of glucose into gluconic acid with glucose oxidase, phosphorylation of sugars using HK, and the like. Among them, the phosphorylation of sugars with HK is most preferred since the materials and reaction product participating in the selective removal of sugars do not adversely affect the quantitative determination of 1,5-AG and the reaction can be completed in a short period of time.

As the enzyme for the phosphorylation of sugars including conversion of glucose into glucose-6-phosphate, it is preferred to use HK classified to be EC 2.7.1.1 according to the International Biochemical Association. In the conversion reaction, ATP and magnesium ions are used in association with the enzyme. As the source for supplying magnesium ions, organic acid salts such as fatty acid salts of magnesium such as magnesium acetates, etc., inorganic acid salts such as halogenates, sulfates, nitrates, phosphates, etc. may be used. Among them, acetates and hydrochlorides and the like are preferred.

According to the present inventor's study, the reaction between 1,5-AG and PROD (hereafter sometimes referred to as a second step reaction) is carried out in the pH range of 7.2 to 8.5, subsequently to the phosphorylation as the first step reaction. It has thus been revealed that even in the presence of an excess of ATP, the reaction between 1,5-AG and PROD efficiently proceeds without PROD being affected by the inhibitory action with ATP and therefore, the phosphorylation as the first step reaction can be rapidly carried out in the pH range of 7.2 to 8.5 using an excess amount of ATP. It has also been revealed that 1,5-AG can further be reacted with PROD as they are, in the pH range of 7.2 to 8.5 in the presence of an excess amount of ATP thereby to continuously perform the first step reaction and the subsequent second step reaction between 1,5-AG and PROD in an extremely short period of time (the process itself was already filed as Japanese Patent Application No. 5-022613).

Furthermore, it has been revealed that also by using PROD especially derived from *Basidiomycetous fungi* No. 52 as PROD, PROD is not inhibited by ATP even in the presence of an excess amount of ATP and hence, the first step reaction and the subsequent second step reaction between 1,5-AG and PROD can be performed in an extremely short period of time (the process itself was already filed as Japanese Patent Application No. 4-324259).

According to the present invention, therefore, the phosphorylation as the first step reaction can be carried out rapidly using an excess amount of ATP. The term "an excess amount of ATP" used in the phosphorylation described above refers to an amount of ATP generally in the range of 2.5 times moles or more, preferably 2.5 to 2,500 times moles, more preferably 10 to 1,000 times moles as much as an amount of glucose suspected to be contained in a sample. Practically, ATP is usually used in a determination system at an amount of 5 mM or more.

Preferred amounts of HK, ATP and magnesium ions which are practically used in the phosphorylation are 5 to 100 U/ml, 5 to 500 mM and 5 to 50 mM, respectively.

The pH of the phosphorylation is preferably in the range of 7.2 to 8.5, more preferably 7.5 to 8.0, as in the pH range for the reaction between 1,5-AG and *Basidiomycetous fungi* No. 52 is used as PROD, it is PROD. Furthermore where PROD derived from preferred to select the pH value in the range of 6 to 9, more preferably in the range of 7.0 to 8.0. As a temperature for the phosphorylation, room temperature is preferred.

The phosphorylation and the aforesaid reaction between maltose in a specimen and α-glucosidase in the first step reaction may be performed in the same reaction system, which is preferred for simplicity of operations.

1,5-AG is measured by the second step reaction in which PROD is acted on 1,5-AG remained in the specimen from which sugars such as glucose, etc. other than 1,5-AG have been selectively removed.

As PROD used in the present invention, a variety of PRODs derived from strains capable of producing PROD may be used without any particular restriction so long as PROD can be classified into EC 1.1.3.10 by the IUPAC-IUB Nomenclature Committee.

For example, there are PROD derived from the strains of microorganisms belonging to the genus polyporous represented by *Polyporus obtusus* ATCC 26733 which is described in Japanese Patent KOKAI (Laid-Open) No. 61-239886, PROD derived from the strains of microorganisms belonging to the genus Coriolus represented by *Coriolus versicolor* IFO 4937 which is described in Japanese Patent KOKAI (Laid-Open) No. 58-43785, PROD derived from the strains of microorganisms belonging to the genus Pleurotus represented by *Pycnoporus coccineus* IFO 4923 which is described in Japanese Patent KOKAI (Laid-Open) No. 62-79780, PROD derived from the strains of microorganisms belonging to the genus Basidiomycetous represented by *Basidiomycetous fungi* No. 52 (FERM P-10106) which is described in Japanese Patent KOKAI (Laid-Open) No. 2-42980, PROD derived from the strains of microorganisms belonging to the genus Daedaleopsis represented by *Daedaleopsis styracina* IFO 4910 which is described in Japanese Patent KOKAI (Laid-Open) No. 58-43785, PROD derived from the strains of microorganisms belonging to the genus Pleurotus represented by *Pleurotus ostreatus* Z-64 (NRRL 12507), PROD derived from the strains of microorganisms belonging to the genus Gloeophyllum represented by *Gloeophyllum sepiarium* Z-41 (NRRL 12506), PROD derived from the strains of microorganisms belonging to the genus Irpex represented by *Irpex lacteus* ATCC 20123 which is described in Japanese Patent KOKAI (Laid-Open) No. 61-177986, PROD derived from the strains of microorganisms belonging to the genus Auricularia represented by *Auricularia polytricha* Z-229 (FERM P-7119), PROD derived from the strains of microorganisms belonging to the genus Coprinus represented by *Coprinus micaceus* ATCC 20122, PROD derived from the strains of microorganisms belonging to the strains of represented by *Trametes cinnabarinus* IFO 6139, etc.

Of these enzymes, preferred are PROD derived from the strains of microorganisms belonging to the genus Polyporus such as *Polyporus obtusus* ATCC 26733 and PROD derived from the strains of microorganisms belonging to the genus Basidiomycetes such as *Basidiomycetes fungi* No. 52, etc.

In the present invention, the phosphorylation is carried out using an excess amount of ATP and then without removing ATP, the enzyme reaction of 1,5-AG in a specimen with PROD can be performed in the pH range of 7.2 to 8.5. By performing the enzyme reaction in the pH range of 7.2 to 8.5, preferably 7.5 to 8.0, PROD is not inhibited by ATP remained in the specimen and PROD shows good reactivity with 1,5-AG. Alternatively, where PROD derived from *Basidiomycetous fungi* No. 52 is used as PROD, this PROD undergoes inhibitory action with ATP only with difficulty so that the phosphorylation can be carried out using an excess amount of ATP and subsequently thereto, the reaction between 1,5-AG and PROD can be continuously carried out as it is. In this case, the pH is set forth in the range of preferably 6 to 9, more preferably 7.0 to 8.0. In the reaction of 1.5-AG with PROD, ATP may exist at the concentration of 5 to 500 mM.

By reacting PROD with 1,5-AG, hydrogen peroxide generates. The hydrogen peroxide is acted on a known peroxidase substrate such as 2,2'-azinobis-(3-ethylbenzothiazoline-6-sulfonic acid), o-phenylenediamine, 5-aminosalicylic acid, 3,3', 5,5'-tetramethylbenzidine, combination of 4-aminoantipyrine and N-ethyl-N-(2-hydroxysulfopropyl)-m-toluidine, using an enzyme classified as EC 1.11.1.7 according to the classification by the International Biochemical Association. Absorbance of the dye thus produced from the substrate is measured.

The peroxidase used for determining hydrogen peroxide is preferably horse radish peroxidase. As the substrate used to produce the dye for measurement of absorbance, the combination of 4-aminoantipyrine and N-ethyl-N- (2-hydroxysulfopropyl)-m-toluidine is preferred. When using the combination of 4-aminoantipyrine and N-ethyl-N-(2-hydroxysulfopropyl)-m-toluidine, its wavelength in the absorbance measurement region is in the range of 500 nm to 800 nm. Within this range, two or more wavelengths may also be used for the measurement.

Preferred amounts of PROD, peroxidase, 4-aminoantipyrine and N-ethyl-N-(2-hydroxysulfopropyl)-m-toluidine used in the reaction described above are in the following ranges, respectively: 5 to 500 U/ml of PROD, 2 to 20 U/ml of peroxidase, 0.1 to 10 mM of 4-aminoantipyrine and 0.1 to 10 mM of N-ethyl-N-(2-hydroxysulfopropyl)-m-toluidine. The pH region effective for the reaction ranges from 7.2 to 8.5, preferably 7.5 to 8.0, or 6 to 9, preferably 7.0 to 8.0.

In the overall reactions for determining 1,5-AG in a specimen, including the first step reaction and the second step reaction, the reaction temperature is maintained generally at room temperature, more specifically between 5° and 40° C., preferably between 25° and 40° C. The reaction time is 2 to 60 minutes, preferably 2 to 30 minutes. During the course of preparing the reaction solution, the reaction as a whole proceeds at pH of, for example, 7.0 to 8.0, preferably 7.5 to 8.0. Therefore, in order to stabilize the reaction solutions of reagents in the pH range of 7.0 to 8.0, preferably 7.5 to 8.0, 6 to 9 at the maximum, phosphate buffer, Tris hydrochloride buffer, PIPES buffer, HEPES buffer, etc. are used as buffer solutions. When HEPES buffer is used, it is preferred to keep its concentration in the range of 50 to 500 mM. For controlling ionic intensity, halogenated alkali metal salts, preferably sodium chloride, etc. may be used.

Where 1,5-AG is assayed according to the method of the present invention, the respective components described above may be incorporated in one solution; for example, a solution containing reagents used for the first step reaction and α-glucosidase as the reagent for converting maltose in a specimen into glucose can be used as a first reagent and, a solution containing PROD and color-forming reagents for measuring hydrogen peroxide as a second reagent solution. Alternatively, in addition to the above method, the respective components may also be used in appropriate combination. These components may be either in a solution form or freeze-dried. Where it is intended to store them over a long period of time, the components may preferably be freeze-dried. It is also possible to add a surface active agent within such a concentration range that does not inhibit the assay reaction. Where the measurement system is lyophilized, a stabilizer may be added in an appropriate amount.

In the present invention, the phosphorylation, enzymatic reaction and color-forming reaction subsequent thereto for measuring the amount of hydrogen peroxide generated can be performed using an automated analysis device.

The automated analysis device or equipment collectively termed in the present invention is specifically exemplified by Model 7050, Model 705, Model 736 and Model 7150 manufactured by Hitachi Ltd., etc. The automated analysis device is not limited to these specific equipments but any devices equivalent thereto are usable in the present invention.

The kit used for the quantitative assay for 1,5-AG of the present invention typically comprises the following reagents, as is clearly noted from the method for quantitative assay described above in detail:

(1) α-glucosidase derived from a microorganism belonging to the genus Bacillus;

(2) HK;

(3) ATP; and, (4) PROD.

In addition to these constituent reagents, the kit may additionally contain the color-forming reagents necessary for determining hydrogen peroxide, buffer solution necessary for controlling pH described above, and the like.

As α-glucosidase derived from a microorganism belonging to the genus Bacillus which is one of the constituent reagents, α-glucosidase derived from *Bacillus stearothermophilus* is preferred.

Preferred examples of PROD include PROD derived from *Polyporous obtusus* and PROD derived from *Basidiomycetous fungi* No. 52. These constituent reagents may be used in a solution form or in a freeze-dried state.

Hereafter the present invention is described in more detail with reference to the examples. Needless to say, the present invention is not deemed to be limited to these examples.

Example 1

Comparison in Maltose Removal Ability

The reaction for removing maltose and glucose was examined using the following specimens as standard ones:

aqueous solutions containing 400, 360, 320, 280, 240, 200, 160, 120, 80, 40 and 0 mg/dl of maltose; aqueous solutions containing 1500, 1350, 1200, 1050, 900, 750, 600, 450, 300, 150 and 0 mg/dl of glucose; and aqueous solutions containing 5.0, 4.5, 4.0, 3.5, 3.0, 2.5, 2.0, 1.5, 1.0, 0.5 and 0 mg/dl of 1,5-AG.

Furthermore, the reactions of quantitative assay for 1,5-AG were compared under the following conditions.

Conditions for Reagents

Reagent 1-A: α-glucosidase which is maltose hydrolase is not added to Reagent 1

Reagent 1-B: 40 KU/l of α-glucosidase derived from Saccharomyces sp. (Toyobo Code No. AGH-201) is added to Reagent 1

Reagent 1-C: 40 KU/l of glucoamylase derived from Rhizopus sp. (Toyobo Code No. AGH-111) is added to Reagent 1

Reagent 1-D: 40 KU/l each of α-glucosidase derived from Saccharomyces sp. and glucoamylase derived from Rhizopus sp. are added to Reagent 1

Reagent 1-E: 40 KU/l of α-glucosidase derived from *Bacillus stearothermophilus* (Toyobo Code No. AGH-211) is added to Reagent 1

Other common reagents and Reagent 2 have the following compositions.

| Common compositions in Reagents 1-A, 1-B, 1-C, 1-D and 1-E: | |
| --- | --- |
| HEPES | 200 mM |
| Sodium chloride | 150 mM |
| Magnesium acetate | 10 mM |
| N-Ethyl-N-(2-hydroxysulfopropyl)-m-toluidine | 1 mM |
| Peroxidase | 5 KU/l |
| Hexokinase | 20 KU/l |
| ATP | 100 mM |
| pH 7.5 | |
| Composition of Reagent 2 | |
| HEPES | 200 mM |
| Sodium chloride | 150 mM |
| 4-Aminoantipyrine | 4 mM |
| PROD derived from *Plyporus obtusus* | 62.5 KU/l |
| pH 7.5 | |

The reaction conditions were set to use 7 μl of standard specimen, 280 μl of Reagent 1 and 70 μl of Reagent 2, and perform the assay at a major wavelength of 546 nm and a side wavelength of 700 nm by 2 point assay using automated analysis device of Hitachi Model 7150.

Figure 2:
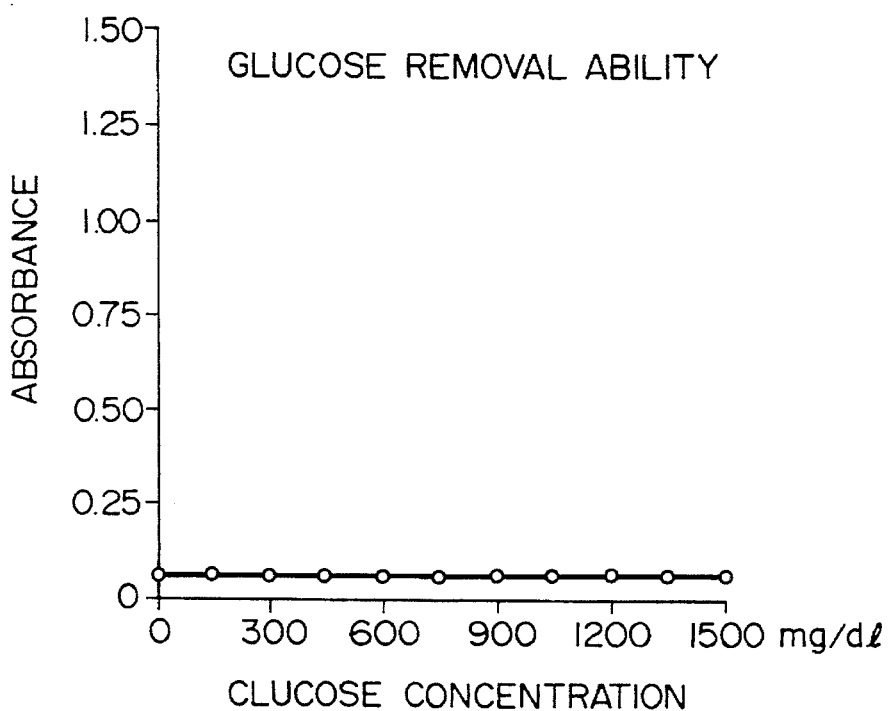
FIG. 2 is a graph showing glucose removal ability where Reagent 1-A is used.
Figure 3:
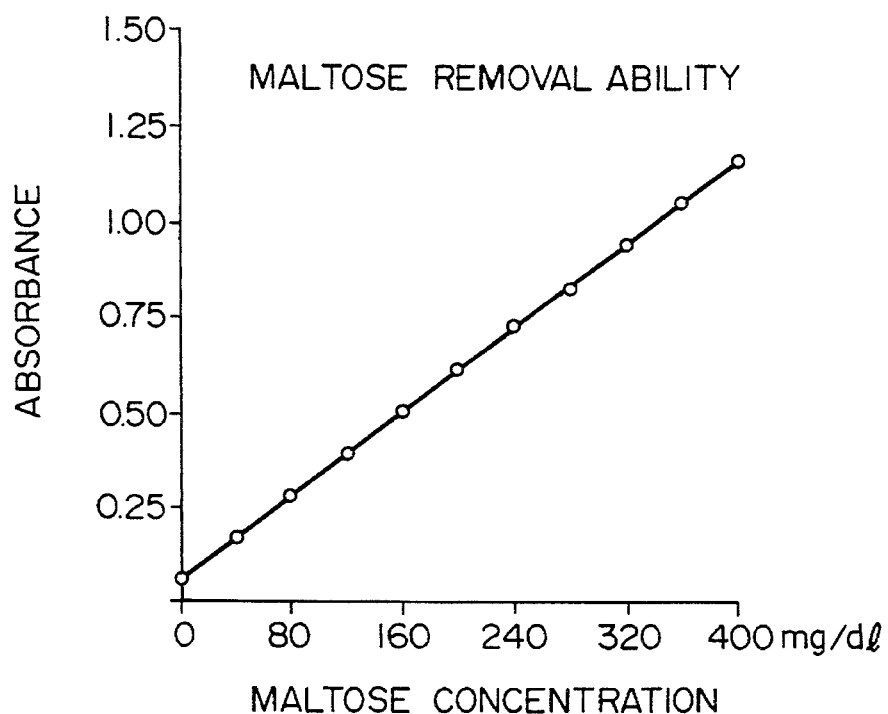
FIG. 3 is a graph showing influence of maltose where Reagent 1-A is used.

FIGS. 1 to 3 show the results obtained using Reagent 1-A (no maltose hydrolase is added).

Figure 4:
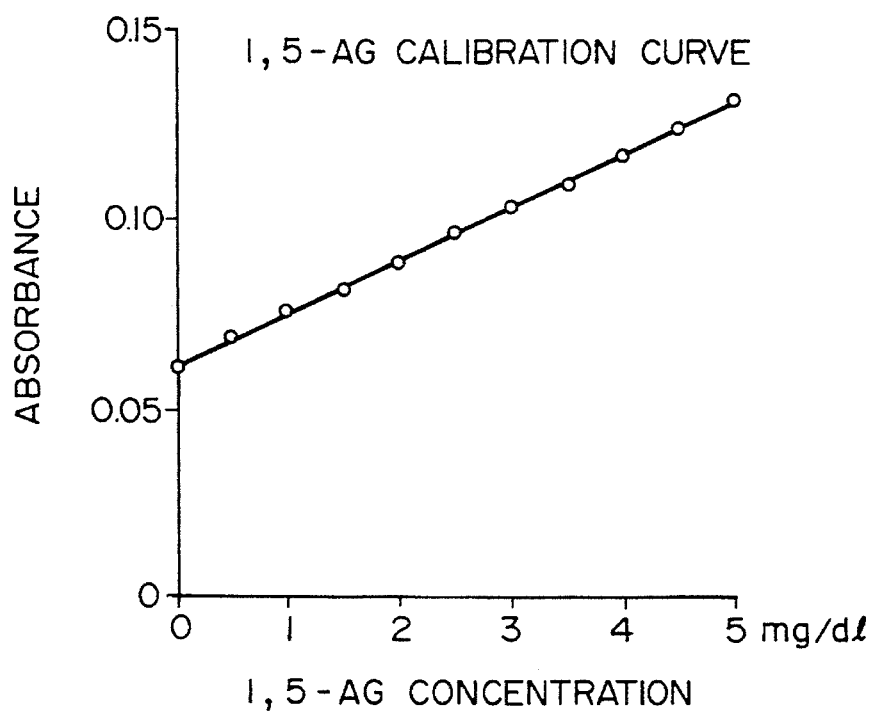
FIG. 4 is a graph showing quantitative property of 1,5-AG where Reagent 1-B (40 KU/l of α-glucosidase derived from Saccharomyces sp. is added) is used.
Figure 5:
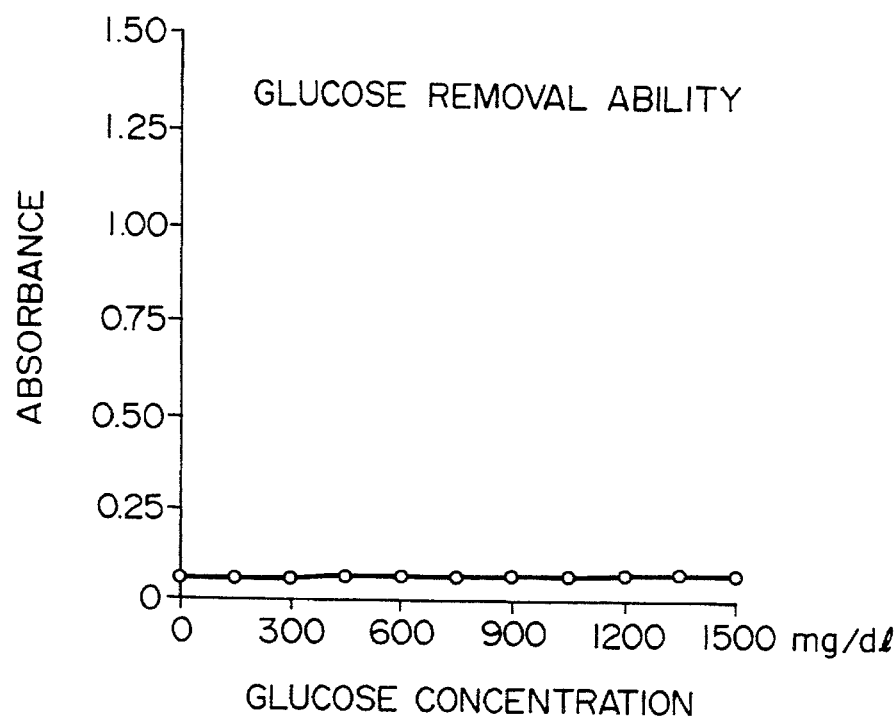
FIG. 5 is a graph showing glucose removal ability where Reagent 1-B is used.
Figure 6:
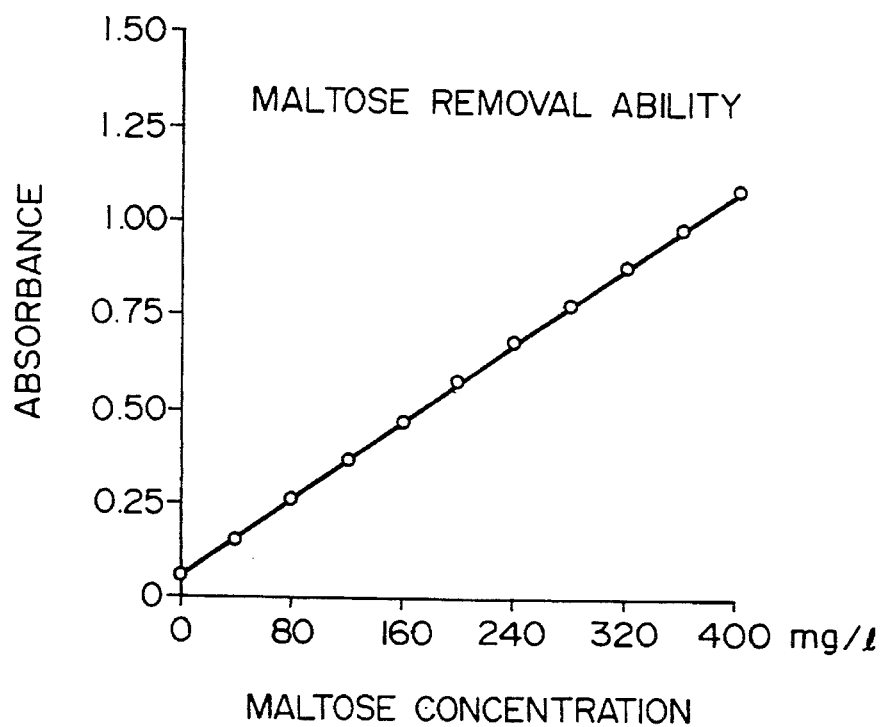
FIG. 6 is a graph showing residual degree of maltose where Reagent 1-B is used.

FIGS. 4 to 6 show the results obtained using Reagent 1-B (40 KU/l of α-glucosidase derived from Saccharomyces sp. is added).

Figure 7:
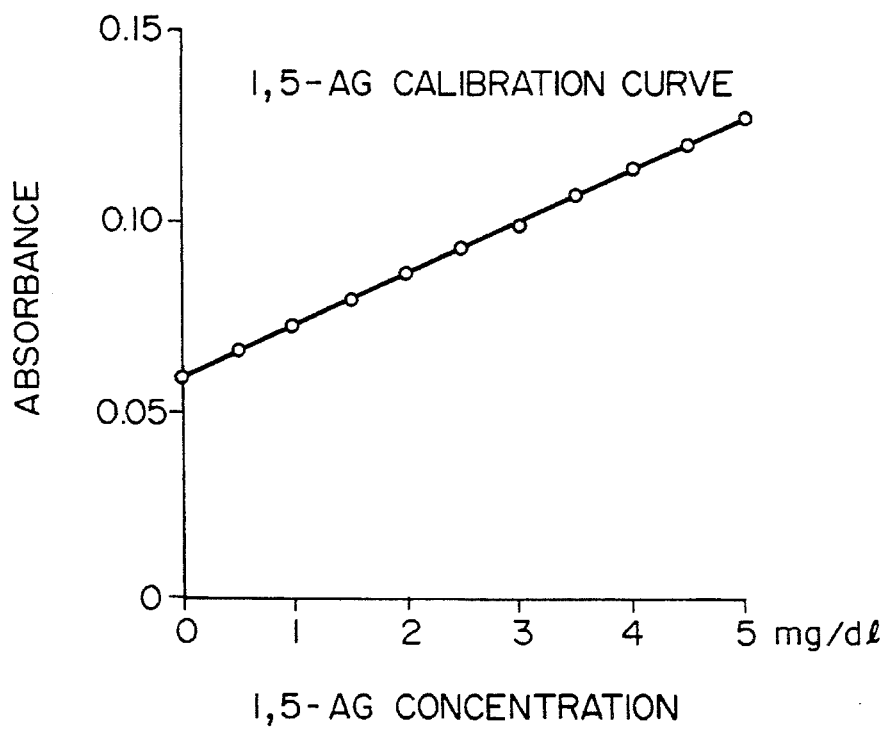
FIG. 7 is a graph showing quantitative property of 1,5-AG where Reagent 1-C (40 KU/l of glucoamylase derived from Rhizopus sp. is added) is used.
Figure 8:
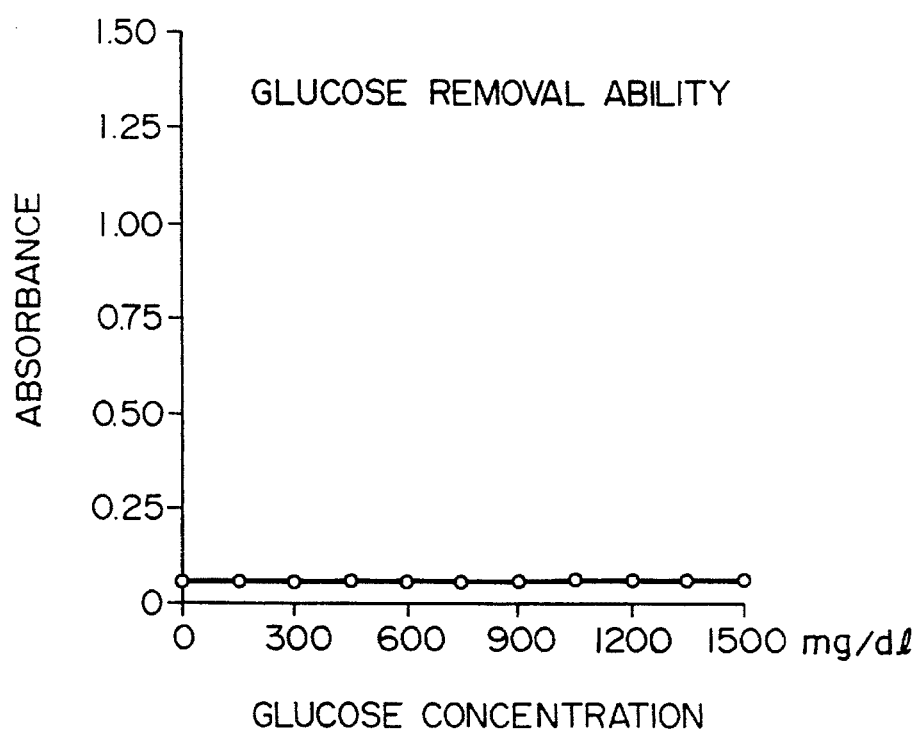
FIG. 8 is a graph showing glucose removal ability where Reagent 1-C is used.
Figure 9:
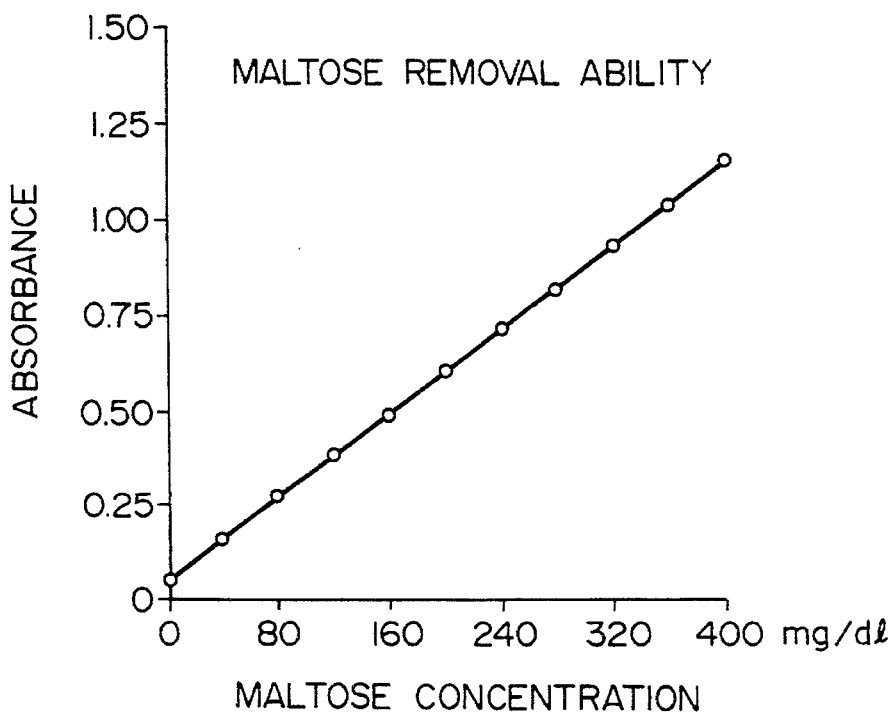
FIG. 9 is a graph showing residual degree of maltose where Reagent 1-C is used.

FIGS. 7 to 9 show the results obtained using Reagent 1-C (40 KU/l of glucoamylase derived from Rhizopus sp. is added).

Figure 10:
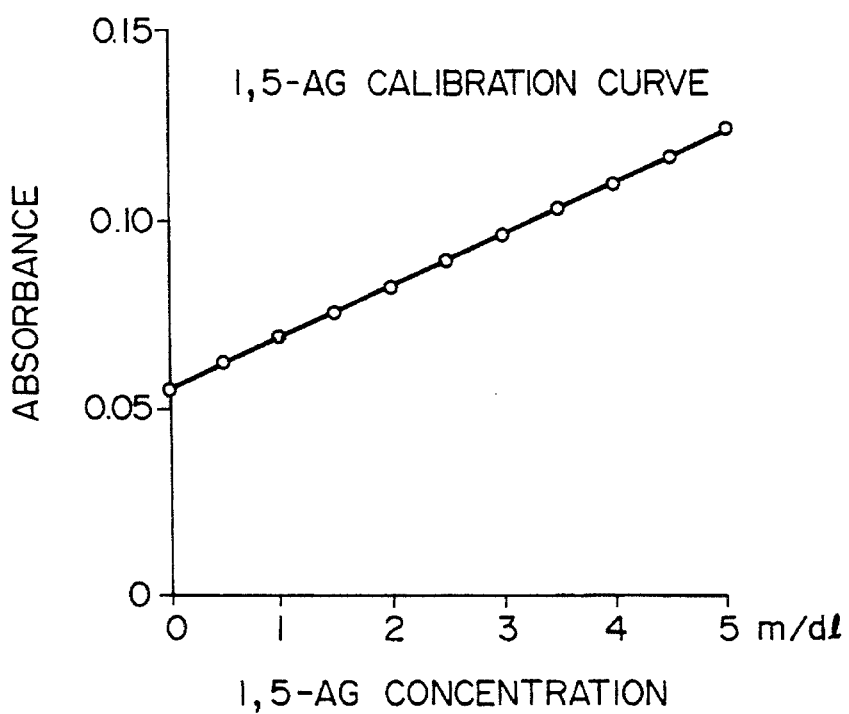
FIG. 10 is a graph showing quantitative property of 1,5-AG where Reagent 1-D (40 KU/l each of α-glucosidase derived from Saccharomyces sp. and glucoamylase derived from Rhizopus sp. are added) is used.
Figure 11:
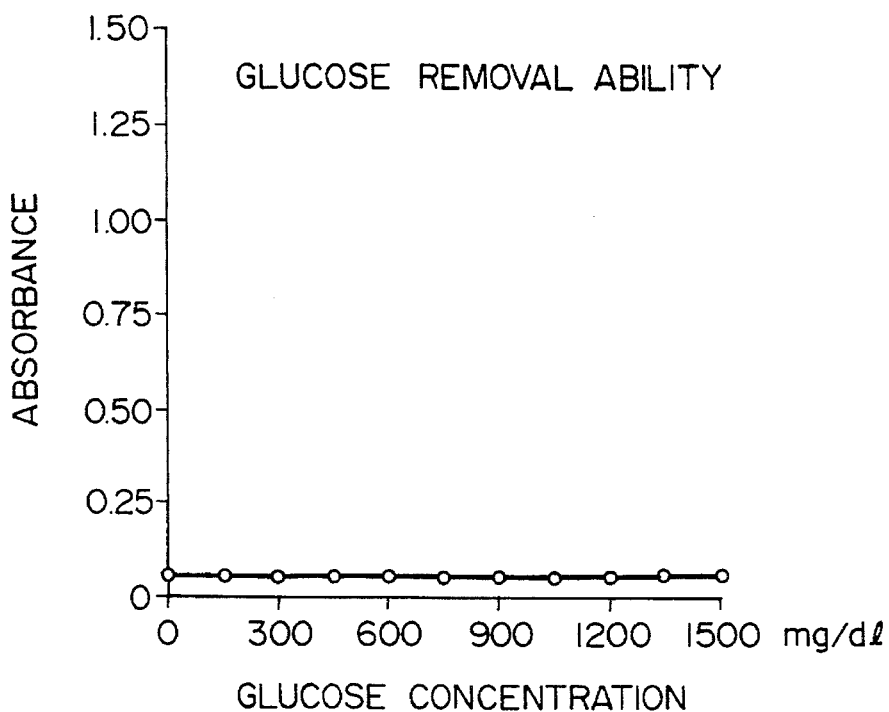
FIG. 11 is a graph showing glucose removal ability where Reagent 1-D is used.
Figure 12:
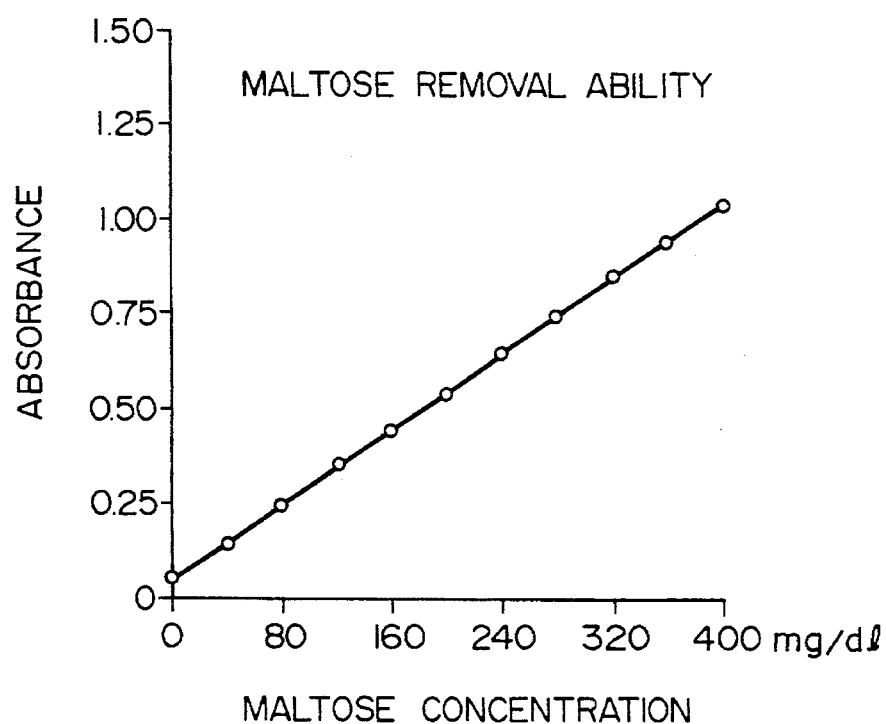
FIG. 12 is a graph showing residual degree of maltose where Reagent 1-D is used.

FIGS. 10 to 12 show the results obtained using Reagent 1-D (40 KU/l each of α-glucosidase derived from Saccharomyces sp. and glucoamylase derived from Rhizopus sp. is added).

Figure 13:
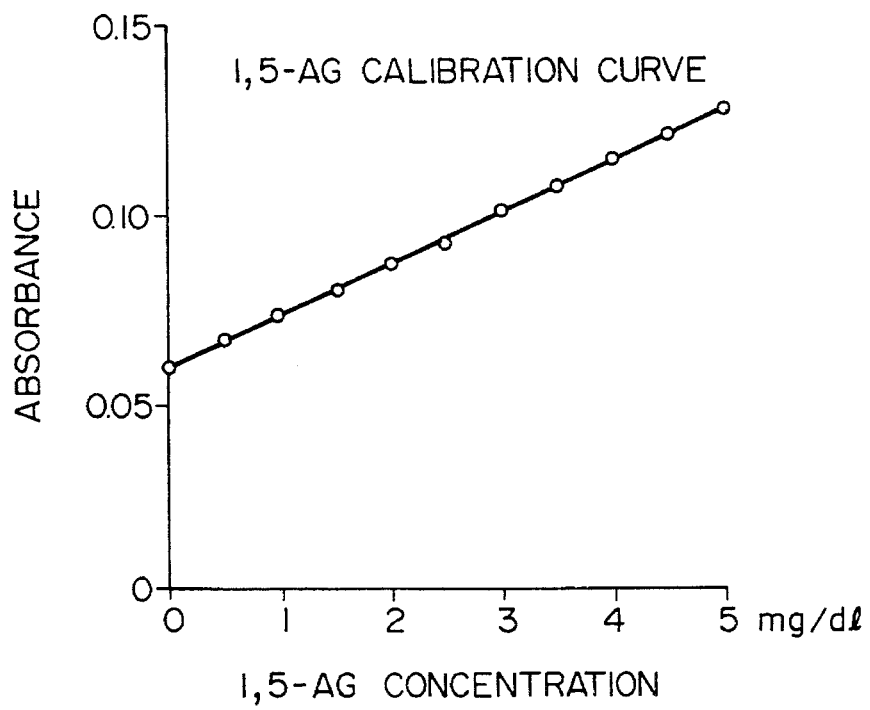
FIG. 13 is a graph showing quantitative property of 1,5-AG where Reagent 1-E (40 KU/l of α-glucosidase derived from *Bacillus stearothermophilus* (Code No. AGH-211, Toyobo)) is used.
Figure 14:
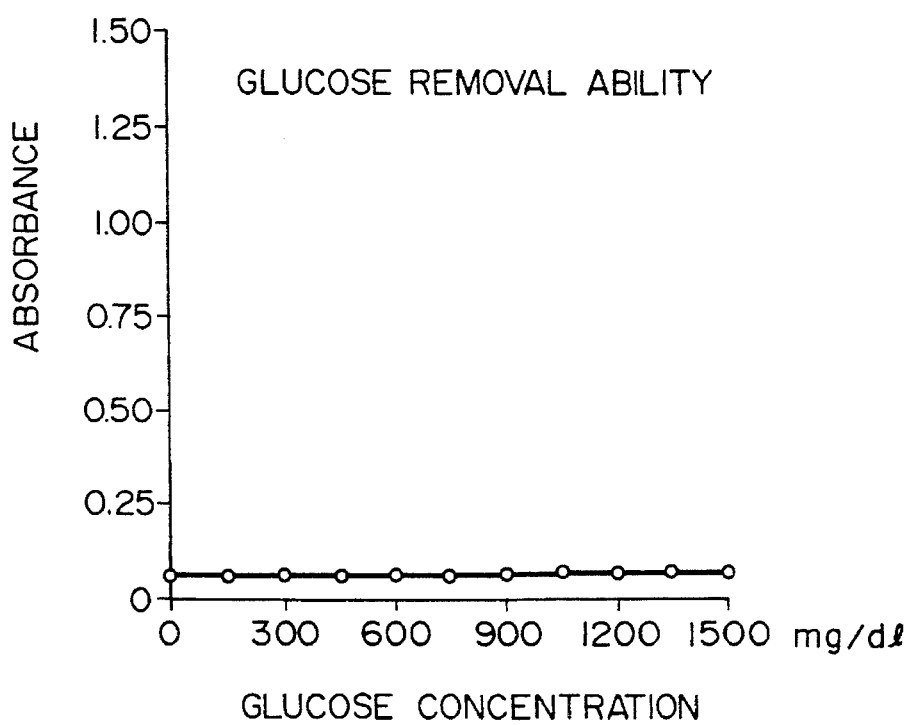
FIG. 14 is a graph showing glucose removal ability where Reagent 1-E is used.
Figure 15:
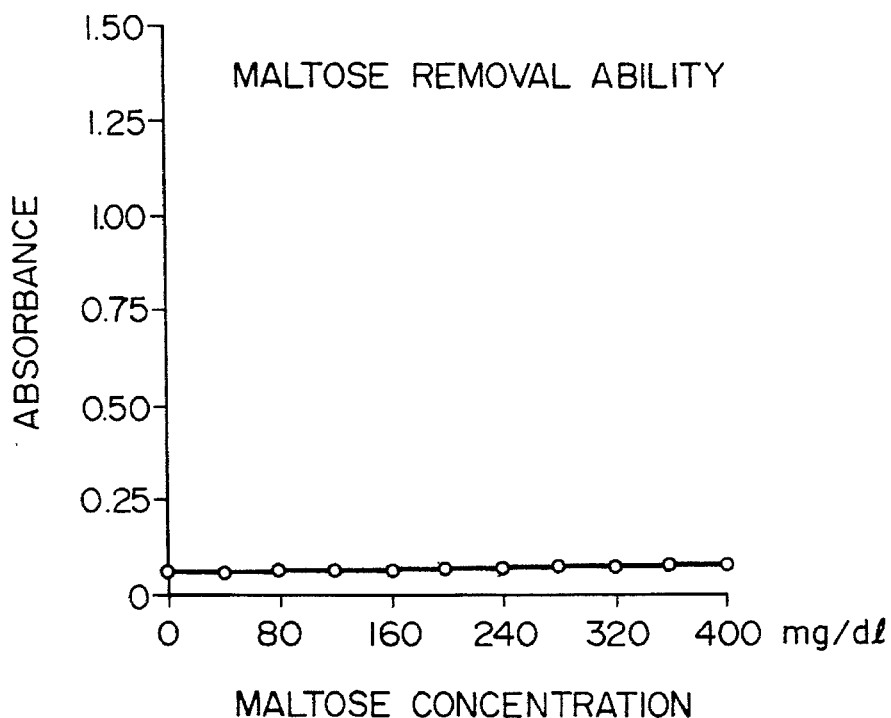
FIG. 15 is a graph showing maltose removal ability where Reagent 1-E is used.

FIGS. 13 to 15 show the results obtained using Reagent 1-E (40 KU/l of α-glucosidase derived from *Bacillus stearothermophilus* (Toyobo Code No. AGH-211) is added).

As shown in FIG. 1, where α-glucosidase as maltose hydrolase was added to Reagent 1, a good linearity passing at the origin up to 5 mg/dl is shown when 1,5-AG is reacted; when glucose was reacted, almost the same absorbance as in reagent blank up to 1500 mg/dl was obtained. As shown in FIG. 3, however, remarkable reaction absorbance was obtained when maltose was reacted. This means that maltose was assayed as 1,5-AG.

As shown in FIGS. 4 to 6, where 40 KU/l of α-glucosidase derived from Saccharomyces sp. was added to Reagent 1, the quantitative property of 1,5-AG and glucose removal ability are as in the case of adding none and almost the same results were obtained also in the case where maltose was reacted. The results reveal that maltose cannot be removed by the α-glucosidase derived from saccharomyces sp.

As shown in FIGS. 7 to 9, where 40 KU/l of glucoamylase derived from Rhizopus sp. was added, the quantitative property of 1,5-AG and glucose removal ability showed the same results as in the case of adding none, as is noted in the case where 40 KU/l of α-glucosidase derived from Saccharomyces sp. was added. The remarkable reaction absorbance when maltose was reacted was not eliminated. The results reveal that maltose cannot be removed even by the glucoamylase derived from Rhizopus sp.

As shown in FIGS. 10 to 12, where 40 KU/l each of α-glucosidase derived from Saccharomyces sp. and glucoamylase derived from Rhizopus sp. were added, the results were similar to those obtained using each enzyme singly. The results reveal that maltose cannot be removed even by combination of the two enzymes.

As shown in FIGS. 13 to 15, where 40 KU/l of α-glucosidase derived from *Bacillus stearothermophilus* (Toyobo Code No. AGH-211) was added, the quantitative property of 1,5-AG and glucose removal ability showed the same results as in the case of adding none; furthermore, it was possible to maintain the resulting absorbance on almost the same level as in the reagent blank up to 200 mg/dl of maltose. The results indicate that unlike other maltose hydrolase, α-glucosidase derived from *Bacillus stearothermgphilus* (Toyobo Code No. AGH-211) has a high affinity to and reactivity with maltose and can erase endogenous maltose in a short period of time in the case where this enzyme is added to Reagent 1.

Example 2

Confirmation of Maltose Removal Ability

Using as specimens those obtained by supplementing 0 to 200 mg/dl of maltose to sera collected from healthy donor and the patient with diabetes, 1,5-AG was quantitatively determined.

Conditions for Reagent 1 are as shown below.

| Composition of Reagent 1: | |
|---|---|
| HEPES | 200 mM |
| Sodium chloride | 150 mM |
| Magnesium acetate | 10 mM |
| N-Ethyl-N-(2-hydroxysulfopropyl)-m-toluidine | 1 mM |
| Peroxidase | 5 KU/l |
| Hexokinase | 20 KU/l |
| ATP | 100 mM |
| α-Glucosidase derived from Bacillus stearothermophilus (Toyobo Code No. AGH-211) | 0 or 40 or 80 KU/l |
| pH 7.5 | |

Reagent 2 was measured under the same conditions as in Example 1. That is, comparison was made between the case where α-glucosidase derived from *Bacillus stearothermophilus* (Toyobo Code No. AGH-211) was not added and the case where 40 KU/l or 80 KU/l of the enzyme was added to confirm maltose removal ability.

The reaction conditions were set to use 7 μl of standard specimen, 280 μl of Reagent 1 and 70 μl of Reagent 2, and perform the assay at a major wavelength of 546 nm and a side wavelength of 700 nm by 2 point assay using automated analysis device of Hitachi Model 7150.

Figure 16:
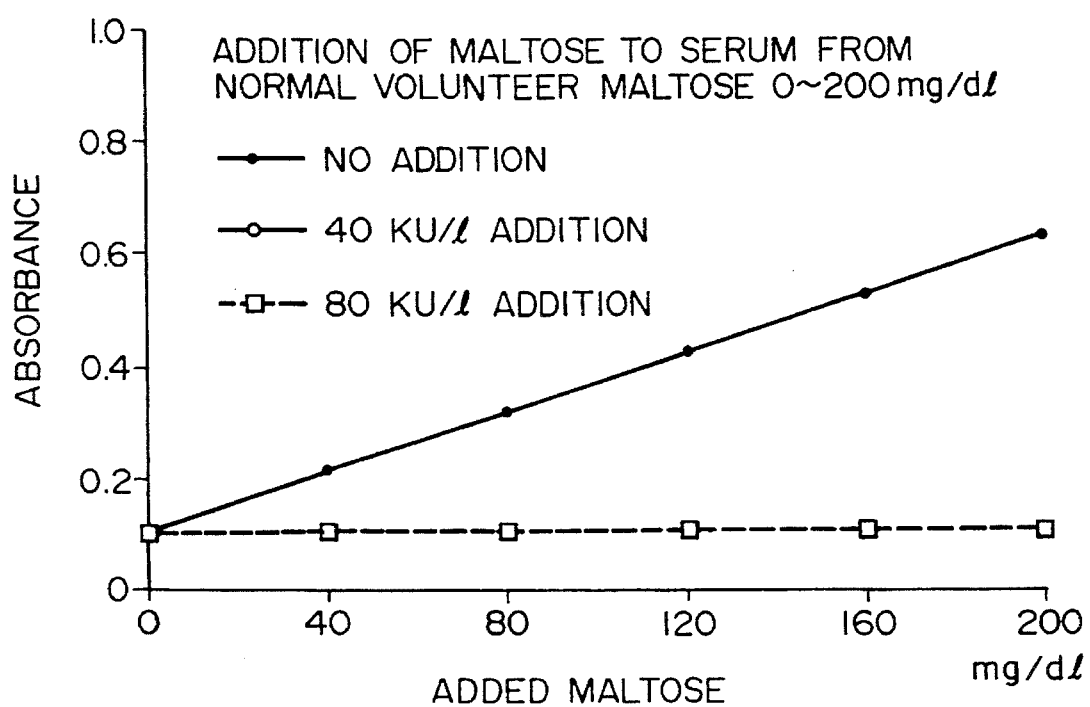
FIG. 16 is a graph showing maltose removal ability in the present invention where maltose is supplemented to the serum collected from volunteer.

FIG. 16 shows the results obtained by the assay for 1,5-AG using as specimens those obtained by supplementing 0 to 200 mg/dl of maltose to the serum collected from healthy donor. In the case where α-glucosidase derived from *Bacillus stearothermophilus* (Toyobo Code No. AGH-211) was not added, marked positive error caused by maltose was noted; in spite, it was confirmed that where 40 KU/l or 80 KU/l of the enzyme was added, the influence of maltose was avoided.

Figure 17:
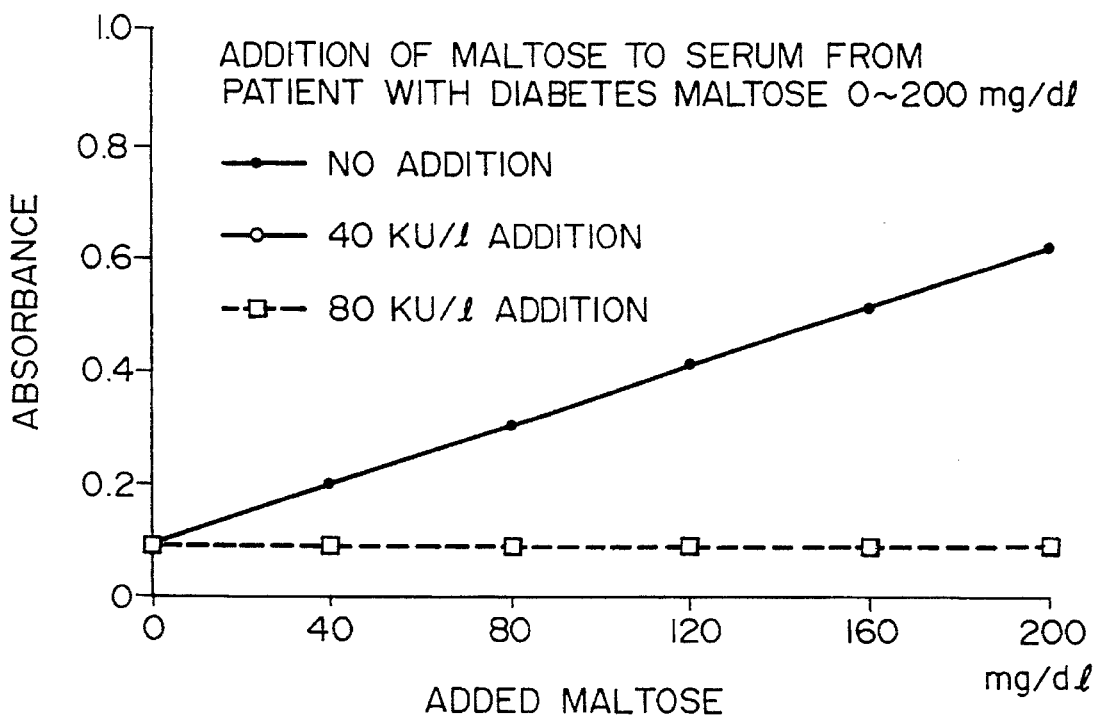
FIG. 17 is a graph showing maltose removal ability in the present invention where maltose is supplemented to the serum collected from the patient with diabetes.

FIG. 17 shows the results obtained by the assay for 1,5-AG using as specimens those obtained by supplementing 0 to 200 mg/dl of maltose to the serum collected from the patient with diabetes. In the case where α-glucosidase derived from *Bacillus stearothermophilus* (Toyobo Code No. AGH-211) was not added, marked positive error caused by maltose was noted; in spite, it was confirmed that where 40 KU/l or 80 KU/l of the enzyme was added, the influence of maltose was almost completely avoided, as in the case that maltose was supplemented to the serum from healthy donor.

Example 3

Comparison with Column Enzyme Method in Maltose Removal Ability in the Case of Using PROPD Derived from *Plyporus Obtusus*

Using as specimens those obtained by supplementing 0 to 200 mg/dl of maltose to sera collected from healthy donor and the patient with diabetes, 1,5-AG was quantitatively determined by each of the method of the present invention and the column enzyme method in a manner similar to Example 2. The column enzyme method was conducted in the manner described in the manual using LANA AG (registered trademark) manufactured by Nippon Kayaku Co., Ltd.

Figure 18:
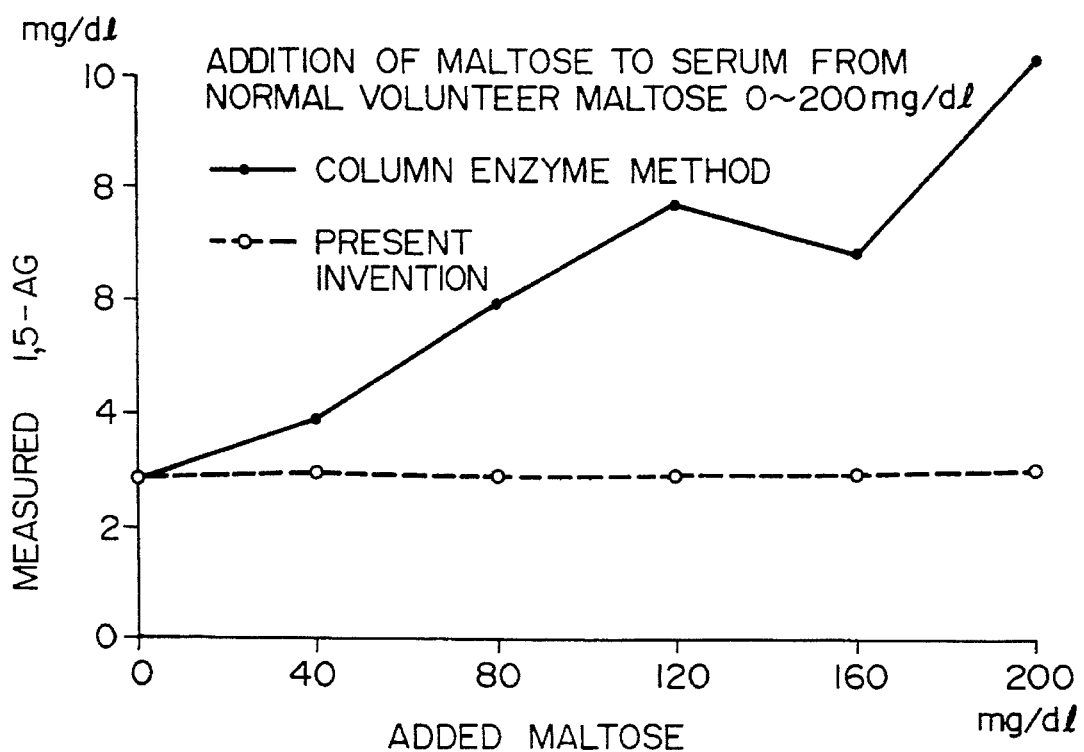
FIG. 18 is a graph showing comparison in maltose removal ability between the column enzyme method and the present invention where maltose is supplemented to the serum collected from volunteer.

FIG. 18 shows the results obtained by the assay for 1,5-AG using as specimen those obtained by supplementing 0 to 200 mg/dl of maltose to the serum collected from healthy donor. For the purpose of comparison in efficiency, the results of the present invention obtained by supplementing 80 KU/l of α-glucosidase derived from *Bacillus stearothermophilus* (Toyobo Code No. AGH-211) shown in Example 2 are also shown. In the column enzyme method, extremely remarkable positive error due to maltose was noted, whereas in the method of the present invention, the positive error due to maltose was almost completely avoided.

Figure 19:
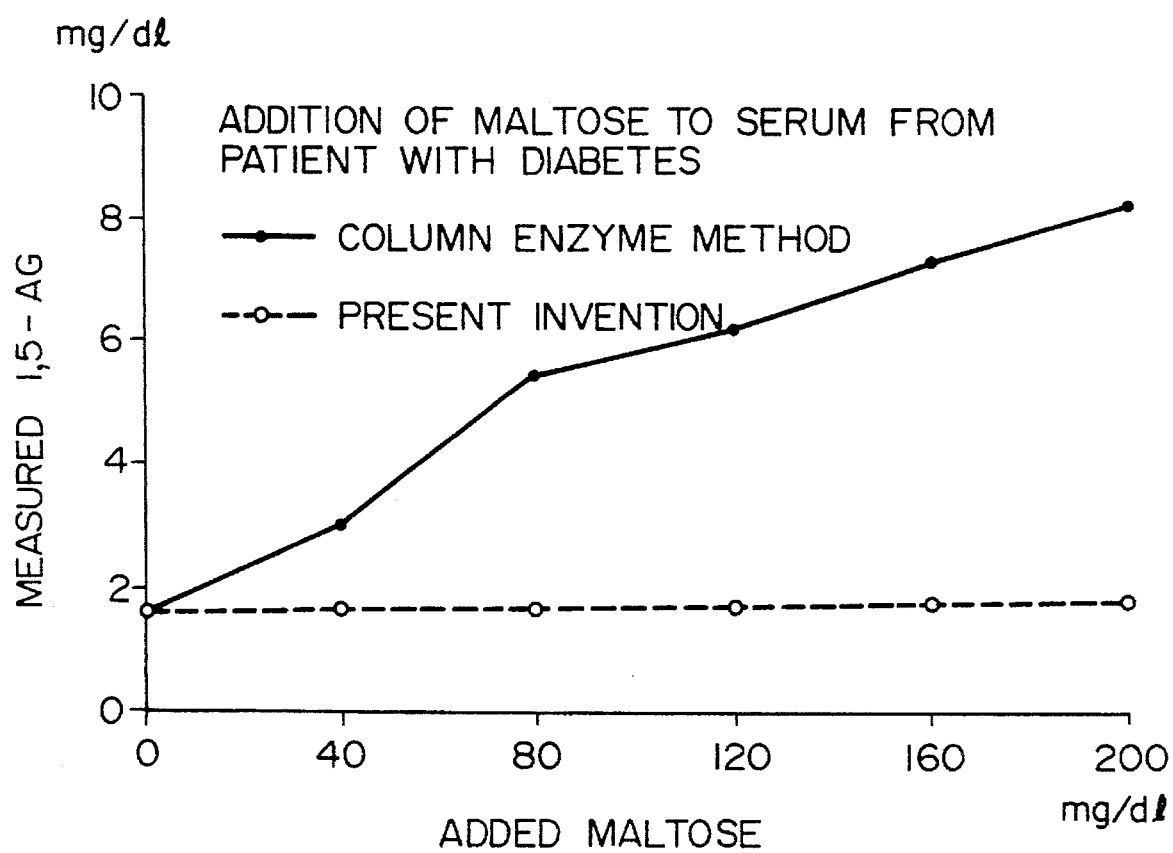
FIG. 19 is a graph showing comparison in maltose removal ability between the column enzyme method and the present invention where maltose is supplemented to the serum collected from the patient with diabetes.

FIG. 19 shows the results obtained by the assay for 1,5-AG using as specimen those obtained by supplementing 0 to 200 mg/dl of maltose to the serum collected from the patient with diabetes. As is noted in the case that maltose was supplemented to the serum collected from healthy donor, extremely remarkable positive error due to maltose was noted also in the column enzyme method; whereas in the method of the present invention, the positive error due to maltose was almost completely avoided.

Example 4

Comparison Between the Present Invention and the Column Enzyme Method in Maltose Removal Ability in the Case of Using PROD Derived from *Basidiomycetous fungi* No. 52

Using as specimens those obtained by supplementing 0 to 200 mg/dl of maltose to sera collected from healthy donor and the patient with diabetes, 1,5-AG was quantitatively determined by the method of the present invention and by the column enzyme method, under the same conditions as in Example 3 except that PROD derived from *Basidiomycetous fungi* No. 52 was used in Reagent 2.

Figure 20:
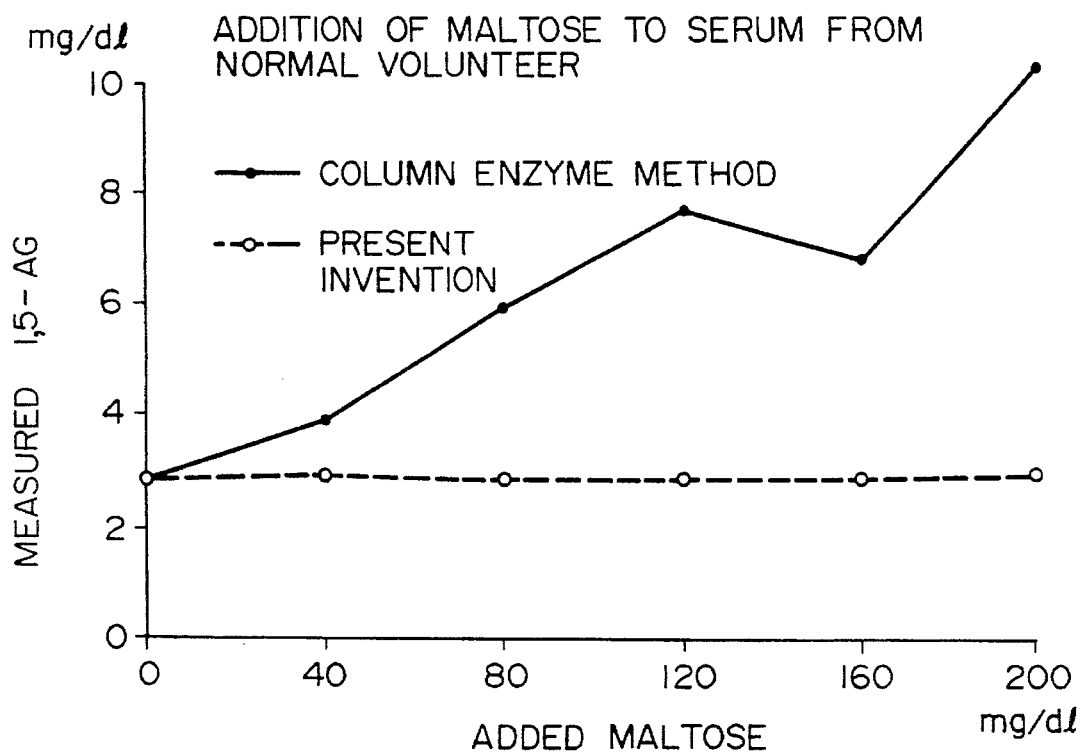
FIG. 20 is a graph showing comparison in maltose removal ability between the column enzyme method and the present invention (PROD derived from *Basidiomycetous fungi* No. 52 is used) where maltose is supplemented to the serum collected from volunteer.
Figure 21:
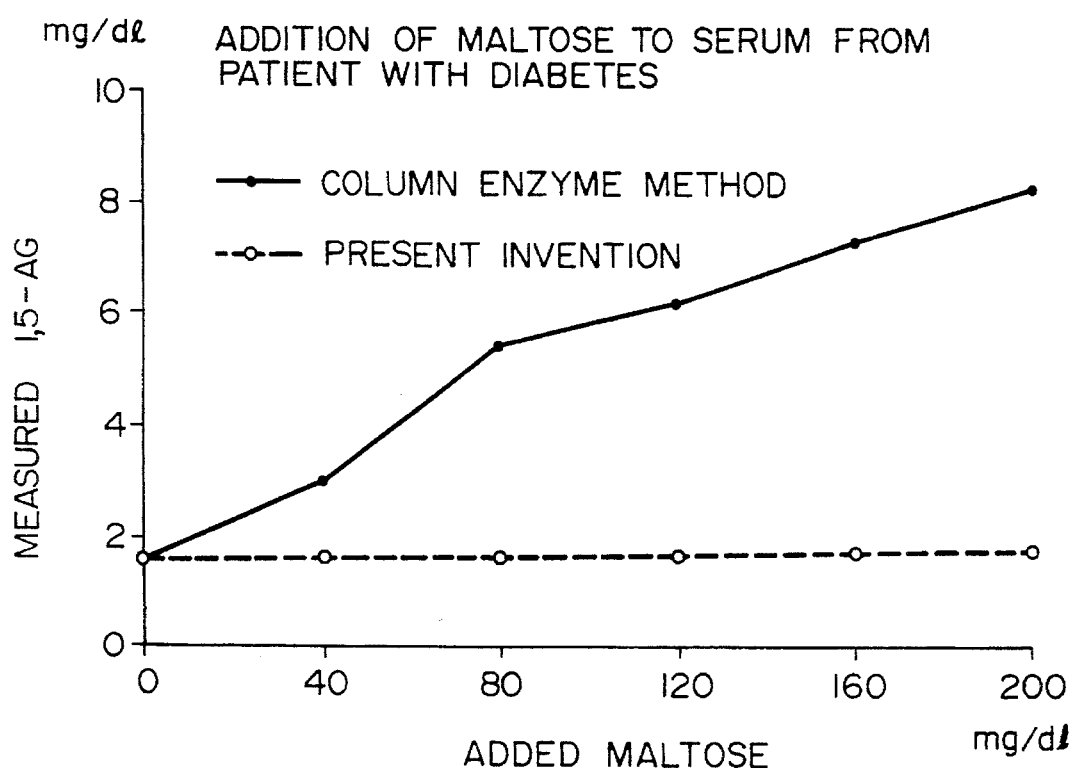
FIG. 21 is a graph showing comparison in maltose removal ability between the column enzyme method and the present invention (PROD derived from *Basidiomycetous fungi* No. 52 is used) where maltose is supplemented to the serum collected from the patient with diabetes.

FIGS. 20 and 21 shows the results obtained by the assay for 1,5-AG using as specimen those obtained by supplementing 0 to 200 mg/dl of maltose to the serum collected from healthy donor, and to the serum collected from the patient with diabetes, respectively.

As in the case of Example 3, extremely remarkable positive error due to maltose was noted in the column enzyme method; whereas in the method of the present invention, the positive error due to maltose was almost completely avoided.

As shown in the foregoing Examples, the method of quantitative assay for 1,5-AG according to the present invention is suited for applying to an automated analysis device and, can avoid the influence due to endogenous maltose. That is, according to the method of the present invention, 1,5-AG can be assayed without influence of maltose using an automated device which was impossible by conventional methods. In addition, a large number of specimens can be handled rapidly and accurately also by assaying many clinical test items.

What is claimed is:

1. In a method for the quantitative assay of 1,5-anhydroglucitol in a specimen derived from human blood, blood serum or blood plasma, wherein maltose in the specimen is converted into glucose by the action of α-glucosidase derived from a microorganism belonging to the genus Bacillus in a first step; said glucose is phosphorylated with a phosphorylating enzyme to selectively remove the glucose and sugars other than 1,5-anhydroglucitol present in the specimen in a second step; and 1,5-anhydroglucitol in the specimen is reacted with a pyranose oxidase in a third step; the improvement of:

performing the three steps in a single reaction zone, at a pH range of from 7.2 to 8.5, at a temperature of from about 5° to 40° C. over a period of from about 2 to 30 minutes, said second step taking place in the presence of an excess amount of adenosine-5'-triphosphate.

2. A method of quantitative assay for 1,5-anhydroglucitol according to claim 1; wherein said pyranose oxidase is derived from *Polyporus obtusus*.

3. A method of quantitative assay for 1,5-anhydroglucitol according to claim 1 wherein 1,5-anhydroglucitol is quantitatively assayed based on the amount of hydrogen peroxide generated upon reaction of 1,5-anhydroglucitol in the specimen with said pyranose oxidase.

4. A method of quantitative assay for 1,5-anhydroglucitol according to claim 1, wherein said glucose is phosphorylated by hexokinase and an excess amount of adenosine-5'-triphosphate.

5. In a method for the quantitative assay of 1,5-anhydroglucitol in a specimen derived from human blood, blood serum or blood plasma, wherein maltose in the specimen is converted into glucose by the action of α-glucosidase derived from a microorganism belonging to the genus Bacillus in a first step; said glucose is phosphorylated with a phosphorylating enzyme to selectively remove the glucose and sugars other than 1,5-anhydroglucitol present in the specimen in a second step; and 1,5-anhydroglucitol in the specimen is reacted with a pyranose oxidase in a third step; the improvement of:

performing the three steps in a single reaction zone, at a pH range of from 6 to 9, at a temperature of from about 5° to 40° C., over a period of from about 2 to 30 minutes, said second step taking place in the presence of an excess amount of adenosine-5'-triphosphate and said pyranose oxidase of said third step being derived from *Basidiomycetous fungi* No. 52.

6. A method of quantitative assay for 1,5-anhydroglucitol according to claim 5, wherein 1,5-anhydroglucitol is quantitatively assayed based on the amount of hydrogen peroxide generated upon reaction of 1,5-anhydroglucitol in the specimen with said pyranose oxidase.

7. A method of quantitative assay for 1,5-anhydroglucitol according to claim 5, wherein said glucose is phosphorylated by hexokinase and an excess amount of adenosine-5'-triphosphate.

* * * * *